United States Patent

Dingerdissen et al.

Patent Number: 5,817,871
Date of Patent: Oct. 6, 1998

[54] PREPARATION OF AMINES

[75] Inventors: Uwe Dingerdissen, Seeheim-Jugenheim; Günter Lauth, Lübeck; Andreas Henne, Neustadt; Peter Stops, Altrip; Karsten Eller; Eugen Gehrer, both of Ludwighshafen, all of Germany

[73] Assignee: BASF Aktiengesellschaft, Ludwigshafen, Germany

[21] Appl. No.: 921,769

[22] Filed: Aug. 15, 1997

Related U.S. Application Data

[63] Continuation of Ser. No. 521,052, Aug. 29, 1995, abandoned.

[30] Foreign Application Priority Data

Sep. 9, 1994 [DE] Germany .......................... 44 31 093.3

[51] Int. Cl.⁶ ................................................ C07C 209/60
[52] U.S. Cl. .......................................................... 564/485
[58] Field of Search ............................ 564/485; 502/202, 502/214, 235

[56] References Cited

U.S. PATENT DOCUMENTS

| | | | |
|---|---|---|---|
| 4,929,728 | 5/1990 | Taglieber et al. | 564/485 |
| 4,929,758 | 5/1990 | Taglieber et al. | |
| 4,929,759 | 5/1990 | Taglieber et al. | |

FOREIGN PATENT DOCUMENTS

| | | |
|---|---|---|
| 39918 | 11/1981 | European Pat. Off. . |
| 3634247 | 7/1987 | Germany . |
| 17995 | 9/1993 | WIPO . |

*Primary Examiner*—Allen J. Robinson
*Assistant Examiner*—Barbara Badio
*Attorney, Agent, or Firm*—John H. Shurtleff

[57] ABSTRACT

A process for preparing an amine by catalytic reaction of an olefin with ammonia or a primary or secondary amine by contacting a mixture of the reactants in a reactor at 200° to 400° C. and an elevated pressure up to 700 bar in the presence of a catalyst consisting essentially of an X-ray amorphous (non-crystalline) mesoporous catalyst, some of which may have a microporous non-crystalline content. The catalyst has the composition $$a\, MO_2 * b\, Q_2O_3 * c\, P_2O_5$$

where Q is at least one of the trivalent elements aluminum, boron, chromium, iron or gallium, and M is at least one of the tetravalent elements silicon, titanium or germanium. The molar ratio of a:b is from 0.5:1 to 1000:1 and the molar ratio of c:b is from 0 to 2:1. As prepared and used in the process, this non-crystalline catalyst has a specific BET surface area of from 200 to 1000 m²/g.

7 Claims, No Drawings

PREPARATION OF AMINES

This application is a continuation of application Ser. No. 08/521,052 filed Aug. 29, 1995, now abandoned.

The present invention relates to a process for preparing amines by reaction of olefins with ammonia or primary or secondary amines at elevated temperatures and pressures in the presence of an X-ray amorphous and non-crystalline catalyst which has an essentially mesoporous and optionally partly microporous structure, e.g. as prepared from an amorphous gel by the sol-gel method followed by calcination of the gel in at least one step at a temperature of from 400° to 600° C. in an oxidizing atmosphere.

The addition of ammonia, or amines which react in a similar way, to olefins in the presence of zeolitic catalysts, in particular boron, aluminum and iron silicate zeolites of the pentasil type as active and long-life catalysts is known from DE-A-33 26 579, DE-A-33 27 000 and DE-A-36 34 247.

A disadvantage of zeolite catalysis is the relatively complicated preparation of the pentasil zeolites by hydrothermal crystallization. The selective synthesis of a molecular sieve requires exact adherence to many parameters, such as the crystallization time, the crystallization temperature or the aging steps.

The structure-directing compounds (templates) usually used in a zeolite synthesis have to be removed after the crystallization. The removal of the template is generally achieved by calcination, with the organic compound being oxidatively degraded.

Zeolites have a very narrow pore size distribution. The pore sizes vary from 4 to about 12 Å, depending on the zeolite type.

In a zeolite-catalyzed reaction, only those molecules which are smaller than the pore dimensions have access to the catalytically active centers in the interior of the zeolite. Reactants having larger dimensions are excluded from the interior of the pores.

It is an object of the present invention to overcome the above disadvantages.

We have found that this object is achieved by a novel, improved process for preparing amines of the general formula I $$H-\underset{\underset{R^6}{|}}{\overset{\overset{R^5}{|}}{C}}-\underset{\underset{R^4}{|}}{\overset{\overset{R^3}{|}}{C}}-N\underset{R^2}{\overset{R^1}{\diagup}} \qquad (I)$$

where $R^1, R^2, R^3, R^4, R^5, R^6$ are hydrogen, $C_1$- to $C_{20}$-alkyl, $C_3$- to $C_{20}$-cycloalkyl, $C_4$- to $C_{20}$-alkyl-cycloalkyl, $C_4$- to $C_{20}$-cycloalkyl-alkyl, aryl, $C_7$- to $C_{20}$-alkylaryl, $C_7$- to $C_{20}$-aralkyl and heterocyclic radicals, which comprises reacting olefins of the general formula II $$\underset{R^6}{\overset{R^5}{\diagdown}}C=C\underset{R^4}{\overset{R^3}{\diagup}} \qquad (II)$$

where $R^3$, $R^4$, $R^5$ and $R^6$ are as defined above, with ammonia or primary or secondary amines of the general formula III $$\underset{R^2}{\overset{R^1}{\diagdown}}N-H, \qquad (III)$$

where $R^1$ and $R^2$ are as defined above, at from 200° to 400° C. and pressures of from 1 to 700 bar in the presence of a mesoporous and, optionally, a partly microporous, X-ray-amorphous catalyst having the composition $$a\ MO_2\ *\ b\ Q_2O_3\ *\ c\ P_2O_5 \qquad (IV),$$

where Q is aluminum, boron, chromium, iron or gallium and M is silicon, titanium or germanium, and the molar ratio of a to b is from 0.5:1 to 1000:1 and that of c to b is from 0 to 2:1, and having a specific BET surface area of from 200 to 1000 $m^2/g$.

The process of the invention for preparing amines I can be carried out as follows:

The reaction proceeds on contact of a mixture of an olefin II and an amine III with the mesoporous and, optionally, the microporous, X-ray-amorphous catalysts above described at from 200° to 400° C. and pressures of from 0.01 to 700 bar.

The reaction can be carried out in the liquid phase (suspension, downward flow or upward flow mode) at from 200° to 400° C. and pressures of from 1 to 700 bar either batchwise or preferably continuously. The weight hourly space velocity of the catalyst should generally be from 0.1 to 20 $h^{-1}$, preferably from 0.5 to 5 $h^{-1}$ (g of starting mixture/g of catalyst and hour).

After the reaction, the products formed are isolated from the reaction mixture by conventional techniques, e.g. by distillation; unreacted starting mixture may, optionally, be recycled to the reaction of the invention.

In a particularly preferred embodiment, the gaseous reaction products are introduced into a separation step immediately after leaving the reactor and are subsequently separated into their individual components. Such a separation can be carried out, for example, in a fractionation column. This is advisable to suppress any reverse reaction and to achieve a high conversion.

Catalysts which are very suitable for the amination reaction according to the invention are amorphous catalysts having a chemical composition of the formula IV which have been prepared from an amorphous gel by the sol-gel method.

Catalysts of this type have a high surface area and a high concentration of acid centers; in comparison with zeolites they are relatively simple to prepare, especially because their preparation does not require a hydrothermal treatment step.

The catalysts of the invention are essentially mesoporous; therefore more voluminous reactants can also penetrate into the pore system and react.

Preparation of the Gels of the Invention

The gels of the invention can be prepared by hydrolysis of a synthesis mixture which contains a solvent and additionally at least the following components:

a soluble, hydrolyzable Q compound, and a soluble, hydrolyzable M compound where Q is at least one trivalent element selected from the group consisting of aluminum, boron, chromium, iron, gallium, M is at least one tetravalent element selected from the group consisting of silicon, titanium, germanium.

Particularly suitable catalysts are those having the composition a $SiO_2$ * b $Al_2O_3$, where the molar ratio of a to b is from 0.5:1 to 1000:1, those having the composition a $SiO_2$ * b $B_2O_3$, where the molar ratio of a to b is from 0.5:1 to 1000:1, those having the composition a $SiO_2$ * b $Al_2O_3$ * c $P_2O_5$, where the molar ratio of a to b is from 10:1 to 1000:1 and that of c to b is from 0.5:1 to 2:1.

In addition, the synthesis mixture can contain further components such as, for example, catalysts, further solvents and/or pore-regulating compounds. In particular, a hydrolysis-accelerating catalyst such as an inorganic or organic acid or base, for example an alkali metal hydroxide such as potassium hydroxide or sodium hydroxide, ammonia, a mineral acid such as hydrochloric acid or hydrofluoric acid, an organic acid such as acetic acid, an organic base such as morpholine, an amine or a tetraalkylammonium hydroxide, may be present.

The pH of the synthesis mixture, which has been altered by the added acids or bases, can also significantly influence the pore structure of the gel or the future catalyst.

Apart from the water required for hydrolysis, further solvents such as alcohols, ethers or ketones can be present.

The presence of pore-regulating compounds can also be advantageous. Such compounds are heteroatom-containing organic compounds such as primary, secondary or tertiary amines or their ammonium compounds, alcohols or polyalcohols, ethers or polyethers, carbonyl-containing or carboxyl-containing compounds, phosphonium compounds.

These compounds influence the formation of the pore structure of the gel; their action has been described for aluminosilicate gels, e.g. in Appl. Catal. 12 (1984) 327 to 357.

These pore-regulating compounds are sometimes also described as "templates". In a particular method of using them, these templates are first reacted with the soluble Q and/or M compounds in a first step and only processed to give a gel in a second step [Chemtech (1993) 26 to 31].

The pore-regulating compound can at the same time serve as catalyst for the hydrolysis process, as pH regulator and/or as solvent.

The soluble hydrolyzable M compound can be a germanium, titanium or silicon compound which is at least colloidally soluble in a solvent and after hydrolysis gives the corresponding oxide. The soluble hydrolyzable compound can be inorganic or organic in nature. Preferred M compounds are silicon compounds such as silicates (e.g. sodium silicate), silicic esters (e.g. tetraethyl orthosilicate) and silica sol. The soluble hydrolyzable Q compound can be an aluminum, boron, chromium, iron or gallium compound which is at least colloidally soluble in a solvent and after hydrolysis gives the corresponding oxide. The soluble hydrolyzable compounds can be inorganic or organic in nature. Preferred Q compounds are aluminum and/or boron compounds. Suitable aluminum compounds are, for example, aluminates (e.g. sodium aluminate), aluminum salts (e.g. aluminum sulfate), aluminum hydroxide, aluminum alkoxides (e.g. aluminum triisopropoxide).

Boron compounds which can be used are, for example, boric acid or its esters.

If the gel is to contain phosphorus, suitable soluble phosphorus sources are, for example, phosphoric acids or soluble phosphates.

The synthesis mixture can additionally contain further metals in dissolved form.

Preparation of the Gels

The synthesis mixture contains the above-described constituents in concentrations corresponding to an oxidic composition as in formula IV. This mixture generally transforms into a gel after a time of from a few minutes to a number of days. The gel formation can be accelerated by increasing the temperature. Particular preference is given to forming the gel at a temperature just below the boiling point of the synthesis mixture. After the preparation, the gels are generally dried at from 70° to 150° C., preferably from 100° to 120° C.

The dried gels can be milled to a wide range of particle sizes. Relatively fine powders are obtained by spray drying the gels. It is likewise possible to apply the gels to supports prior to drying and this leads to catalysts having a shell structure.

Calcination of the gels at from 400° to 600° C., preferably from 500° to 580° C., in an oxidizing atmosphere gives the catalysts of the invention which are used in the amination either directly or preferably after an extrusion step.

The calcination can also be carried out in a plurality of steps at different temperatures and in different gas atmospheres. However, at least one of the calcination steps has to be carried out as described above in an oxidizing atmosphere at from 400° to 600° C.

The amorphous materials obtained by calcination of the dried gels have the following properties:

The calcined gels are not crystalline. The X-ray diffraction pattern shows no structure of any kind; the materials are "X-ray-amorphous".

The calcined gels have a large specific surface area. In general, the surface area determined by the BET method [J. Amer. Chem. Soc. 50 (1938) 309 to 319] is greater than 180 $m^2/g$, preferably from 200 to 1000 $m^2/g$.

A characteristic of some of the calcined gels prepared according to the invention is the presence of pores in the size range from 2 to 50 nm, which are known as mesopores. The presence of these mesopores results, in gas adsorption measurements using nitrogen at 77 K, in an adsorption isotherm having a hysteresis loop. The adsorption isotherm of the gels calcined according to the invention has a shape known as type IV [classification of the isotherm shapes, for example, in J. Am. Chem. Soc. 62 (1940) 1723]. A hysteresis loop can be attributed to capillary condensation in the mesopores and is not found in materials which are not mesoporous (e.g. zeolites).

The calcined gels generally also possess micropores (pore size <2 nm).

The pore size distribution of the calcined gels prepared according to the invention is usually significantly broader than in the case of molecular sieves.

Further mesopores and even macropores can be introduced into the catalyst by extruding the gels with or without a binder, by spray drying the gels or applying the gels to supports.

The calcined gels, if they are present in the H form, usually have a distinctly acid character. The acidity can be quantified, for example as described in J. Am. Chem. Soc. 54, (1932) 2721, using indicators.

The gels prepared according to the invention can, after drying at from 100° to 160° C., preferably from 100° to 120° C., and calcination at from 400° to 600° C., preferably from 500° to 580° C., be shaped using a binder to give extrudates of pellets. Suitable binders are various aluminum oxides, preferably boehmite, pseudoboehmite, silicon dioxide, titanium dioxide, zirconium dioxide and clays. After shaping, the extrudates or pressed compacts are dried and calcined.

Very active and selective catalysts are also obtained when the gels are shaped directly after drying with addition of a binder and/or peptizing agent and are subjected to calcination only after shaping.

The gels can also be used as extrudates or pellets without binder, in which case, for example, ethylcellulose, stearic acid, potato starch, formic acid, oxalic acid, acetic acid, nitric acid, ammonia, amines, silica, graphite or mixtures thereof can be used as peptizing agent.

If, owing to its preparation, the gel is not in the catalytically active, acid H form, but, for example, in the sodium form, this can be converted completely or partially into the desired H form by ion exchange, for example using ammonium ions and subsequent calcination or by treatment with acids.

The gels or catalysts obtained can be modified after calcination. The modification can comprise, for example, doping or ion exchange with a further metal or thermal treatment in a gas atmosphere, e.g. in steam or hydrogen.

If deactivation caused by coke deposition occurs in the catalysts of the invention, it is advisable to regenerate the catalysts by burning off the coke deposits using air or an air/nitrogen mixture at from 400° to 550° C. This restores the catalysts to their initial activity.

The catalysts described here can be used either as extrudates or as pellets having a diameter of from 1 to 5 mm or as chips or as fluidized-bed catalysts.

The substituents $R^1$ and $R^2$ and the index n in the compounds of the general formula I, II and III are as defined below:

$R^1$, $R^2$, $R^3$, $R^4$, $R^5$ and $R^6$ independently of one another hydrogen, $C_1$- to $C_{20}$-alkyl, preferably $C_1$- to $C_{12}$-alkyl such as methyl, ethyl, n-propyl, iso-propyl, n-butyl, iso-butyl, sec-butyl, tert-butyl, n-pentyl, iso-pentyl, sec-pentyl, neo-pentyl, 1,2-dimethylpropyl, n-hexyl, iso-hexyl, sec-hexyl, n-heptyl, iso-heptyl, n-octyl, iso-octyl, n-nonyl, iso-nonyl, n-decyl, iso-decyl, n-undecyl, iso-undecyl, n-dodecyl and iso-dodecyl, particularly preferably $C_1$- to $C_4$-alkyl such as methyl, ethyl, n-propyl, iso-propyl, n-butyl, iso-butyl, sec-butyl and tert-butyl, $C_1$- to $C_{20}$-cycloalkyl, preferably $C_3$- to $C_8$-cycloalkyl such as cyclopropyl, cyclobutyl, cyclopentyl, cyclohexyl, cycloheptyl and cyclooctyl, particularly preferably cyclopentyl, cyclohexyl and cyclooctyl, $C_4$- to $C_{20}$-alkyl-cycloalkyl, preferably $C_6$- to $C_{20}$-alkylcycloalkyl such as 2-methylcyclopentyl, 3-methylcyclohexyl and 4-methylcyclohexyl, $C_4$- to $C_{20}$-cycloalkyl-alkyl, preferably $C_6$- to $C_{20}$-cycloalkylalkyl such as cyclopentylmethyl, cyclohexylmethyl and cyclohexylethyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$- to $C_{20}$-alkylaryl, preferably $C_7$- to $C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $C_7$- to $C_{20}$-aralkyl, preferably $C_7$- to $C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, a heterocyclic radical such as an aromatic or nonaromatic heterocycle containing from one to three hetero atoms such as nitrogen, oxygen and/or sulfur, preferably nitrogen or oxygen.

Preferred examples of olefins II are:

ethene, n-propene, iso-propene, but-1-ene, iso-butene, but-2-ene, diisobutene, cyclopentene, cyclohexene and polyisobutene.

The compound III is preferably ammonia.

Preferred examples of aliphatic amines III are:

methylamine, ethylamine, n-propylamine, iso-propylamine, N-butylamine, iso-butylamine, sec-butylamine, N-2-methyl-2-propylamine, N-3-methyl-1-butylamine, N-hexylamine, N-octylamine, 2-ethylhexylamine, N-tridecylamine, dimethylamine, diethylamine, di-n-propylamine, di-iso-propylamine, di-n-butylamine, di-isobutylamine, di-sec-butylamine, N-methyl-N-n-butylamine, N-ethyl-N-n-butylamine and aniline.

Preferred examples of cyclic amines III are:

pyrrolidine, morpholine and piperidine, dihydropyrrole and tetrahydropyrrole.

The preparation of such starting materials of the formulae II and III is adequately described in standard works (Beilstein, Gmelin).

The amines I are generally valuable building blocks in organic syntheses. Such compounds are particularly important as precursors for drugs and active compounds in herbicides, fungicides and insecticides and as catalysts for organic synthesis or in polymerizations.

EXAMPLES

Preparation of the Catalysts

Catalyst A 0.62 g of boric acid was dissolved in 68.5 g of a 13.35% strength tetrapropylammonium hydroxide solution. The solution was heated to 60° C. and 104.1 g of tetraethyl orthosilicate were added while stirring. After 15 minutes at 60° C., a homogeneous gel was formed, and this is dried at 110° C.

A small sample of the dried gel is calcined at 550° C. in air and characterized: The calcined material is X-ray-amorphous and has a BET surface area of 670 m²/g. The material shows an adsorption isotherm having a hysteresis loop. A pore size distribution in the mesopore range having a distinct maximum at from 30 to 40 Å can be calculated from this isotherm. The chemical composition of the material is approximately $SiO_2 * 0.01\ B_2O_3$.

For use in the amination reaction, the silica gel containing boron oxide is extruded as follows to give a shaped body:

40 g of the dried gel are milled in a ball mill to a size of from 10 to 50 μm. In a compounder, 20 g of pseudoboehmite are added to the comminuted gel and the composition is worked with water and a little formic acid to give a viscous paste.

The paste is extruded, dried at 110° C. for 5 hours and calcined for 8 hours at 550° C. in air.

Catalyst B 6 g of aluminum triisopropoxide were dissolved in 68.5 g of a 15% strength ammonia solution. The solution was heated to 60° C. and 104.1 g of tetraethyl orthosilicate were added while stirring.

After 20 minutes at 60° C., a homogeneous gel was formed, and this is dried at 110° C. A small sample of the dried gel is calcined at 550° C. in air and characterized: the calcined material is X-ray-amorphous, has a BET surface area of 580 m²/g and possesses an adsorption isotherm having a hysteresis loop. The chemical composition of the material is approximately $SiO_2.0.03\ Al_2O_3$.

For use in the amination reaction, the silica gel containing aluminum oxide is extruded to give a shaped body as described for catalyst A.

Catalyst C 10 g of pyrogenic silica (Aerosil®) were dissolved in 235 g of tetrapropylammonium hydroxide (FLUKA, 20% strength). 0.5 g of aluminum hydroxide are added to this solution and the mixture is vigorously stirred.

After slow addition of a total of 200 ml of a 1 molar hydrochloric acid solution, the solution gelled.

The gel was aged at room temperature for 24 hours and subsequently dried at 110° C.

Approximate composition of the material: $SiO_2.0.02\ Al_2O_3$.

For use in the amination reaction, the silica gel containing aluminum oxide is extruded to give a shaped body as described for catalyst A.

Catalyst D 46 g of aluminum triisopropoxide, 23 g of phosphoric acid (85% strength), 12 g of silica sol (15% strength) and 28.7 g of tri-n-propylamine (TPA) were added to 44 g of water while stirring. The mixture was homogenized and treated at 50° C. for 15 minutes, during which time the mixture gelled. The approximate chemical composition of the calcined gel was: $Al_2O_3.0.9\ P_2O_5.0.3\ SiO_2$. For use in the amination reaction, the aluminum phosphate gel containing silicon oxide is extruded to give a shaped body as described for catalyst A.

Catalyst E 88.2 g of sodium aluminate, 45.6 g of sodium hydroxide and 384 g of water were heated to from 60° to 80° C. and stirred using a high-speed stirrer. This solution is admixed quickly with a solution of 360 g of sodium waterglass, 638 g of water and 45.6 g of sodium hydroxide at 100° C. The mixture was homogenized for 5 minutes, during which time the mixture gelled. The gel is subsequently aged for 16 hours at room temperature. The gel is calcined for 16 hours at 550° C. and stirred for 2 hours with a 1 molar ammonium nitrate solution for the purpose of ion exchange. This process is repeated three times, the material being calcined at 550° C. and the ammonium nitrate treatment being repeated.

The approximate chemical composition of the calcined gel was: $SiO_2.0.3\ Al_2O_3$.

For use in the amination reaction, the ion-exchanged silica gel containing aluminum oxide is extruded to give a shaped body as described for catalyst A.

Catalyst F 74 g of pyrogenic silica are suspended in 960 g of a 50% strength hexamethylenediamine solution. This suspension was admixed with a solution of 14 g of boric acid in 80 g of 50% strength hexamethylenediamine solution. The solution was heated while stirring to 60° C., with the mixture gelling after 60 minutes. The gel was aged for 16 hours at room temperature and dried at 110° C.

The approximate chemical composition of the calcined gel was: $SiO_2.0.03\ B_2O_3$.

For use in the amination reaction, the boron-containing $SiO_2$ gel is extruded to give a shaped body as described for catalyst A.

Catalyst G

Catalyst G is obtained by treating 50 g of catalyst C with 140 ml of 0.1N HF for 1 hour under reflux. After filtration and washing with water, it is dried at 110° C. for 16 hours and calcined at 500° C. for 5 hours.

Catalyst H

Catalyst H is obtained by treating 50 g of catalyst C with 2% by weight of $H_3BO_3$. After filtration and washing with water, it is dried at 110° C. for 16 hours and calcined at 500° C. for 5 hours.

Catalyst I

Catalyst I is obtained by treating 50 g of catalyst F with 2% by weight of $H_3BO_3$. After filtration and washing with water, it is dried at 110° C. for 16 hours and calcined at 500° C. for 5 hours.

Catalyst J

Catalyst J is obtained by treating 50 g of catalyst B with 2% by weight of $H_3PO_4$. After filtration and washing with water, it is dried at 110° C. for 16 hours and calcined at 500° C. for 5 hours.

Catalyst K 240 g of tetramethoxysilane $(Si(OCH_3)_4$ are mixed with 21.8 g of trimethyl borate $(B(OCH_3)_3)$ and 60 g of Sokalan CP 10 S® (50% polyacrylic acid in water). After stirring for 30 minutes, 380 g of water and 13 g of 0.1N hydrofluoric acid are added thereto. After a further 15 minutes, the stirring is stopped and the mixture is left to gel fully. The gel is dried for 2 hours at 120° C., subsequently milled and calcined for 12 hours at 350° C.

Extrusion is carried out by a method similar to that for catalyst A, calcination is for 5 hours at 500° C. BET surface area: 326 m²/g.

Catalyst L 36 g of aluminum triisopropoxide are dissolved in 360 g of isopropanol at 70° C. and the solution is then cooled to room temperature. 180 g of tetramethoxysilane, 180 g of water and 7.7 ml of 0.1N hydrofluoric acid are slowly added thereto in this order. After stirring for some time at room temperature, the mixture is heated to 50° C. and fully gelled. The gel was dried for 2 hours at 120° C., subsequently milled and calcined for 12 hours at 350° C.

Extrusion is carried out by a method similar to that for catalyst A, calcination is for 5 hours at 500° C. BET surface area: 228 m²/g.

Catalyst Y (Comparative Catalyst)

Commercial amorphous aluminosilicate (BET: 180 m²/g)

Catalyst Z (Comparative Catalyst)

Aluminum zeolite of the pentasil type ($SiO_2/Al_2O_3=40$)

Examples 1 to 32

The experiments are carried out in a continuous high-pressure apparatus. The reactor volume is 100 ml and heating is by means of Alublock heating. A triple internal temperature measurement is carried out, and the pressure is maintained at 300 bar. The starting material mixture (isobutene and ammonia) is fed in from the top. The catalyst charge is about 60 ml and the remaining reactor volume is filled with inert material (glass spheres, porcelain rings, etc.). The liquid and gaseous products are separately analzyed by gas chromatography. The ammonia to isobutene ratio is 1.5.

TABLE 1

| Example No. | Catalyst | Temperature [°C.] | WHSV (g of starting material/h/g of catalyst) | Yield [%] |
|---|---|---|---|---|
| 1 | A | 270 | 0.7 | 2.8 |
| 2 | A | 270 | 1.5 | 1.4 |
| 3 | A | 270 | 3.0 | 0.8 |
| 4 | A | 300 | 0.7 | 11.4 |
| 5 | A | 300 | 1.5 | 8.8 |
| 6 | A | 300 | 3.0 | 5.8 |
| 7 | B | 270 | 0.2 | 17.0 |
| 8 | B | 270 | 0.5 | 11.7 |
| 9 | B | 270 | 1.0 | 1.5 |
| 10 | B | 300 | 0.7 | 15.2 |
| 11 | B | 300 | 1.5 | 14.8 |
| 12 | B | 300 | 3.0 | 13.4 |
| 14 | C | 270 | 0.7 | 12.2 |
| 17 | C | 300 | 1.5 | 12.6 |
| 19 | D | 270 | 1.5 | 0.5 |
| 20 | D | 300 | 1.5 | 2.1 |
| 21 | E | 270 | 1.5 | 2.6 |
| 22 | E | 300 | 1.5 | 2.2 |
| 23 | F | 270 | 1.5 | 5.4 |
| 25 | G | 270 | 0.7 | 14.1 |
| 26 | H | 270 | 0.7 | 12.4 |
| 27 | I | 270 | 0.7 | 9.4 |
| 28 | J | 270 | 0.7 | 14.3 |
| 29 | Y | 270 | 1.5 | 0.3 |
| 30 | K | 300 | 0.7 | 13 |
| 31 | K | 300 | 1.5 | 10 |
| 32 | K | 300 | 3 | 7 |
| 33 | L | 300 | 0.7 | 12 |
| 34 | L | 300 | 1.5 | 10 |
| 35 | L | 300 | 3 | 7 |
| 36 | Y | 300 | 1.5 | 2.7 |
| 37 | Z | 270 | 1.5 | 16.7 |
| 38 | Z | 300 | 1.5 | 12.9 |

Example 39

The experiments are carried out in a continuous high-pressure apparatus. The reactor volume is 100 ml and heating is by means of Alublock heating. A triple internal temperature measurement is carried out, and the pressure is maintained at 300 bar. The starting material mixture (cyclopentene and ammonia) is fed in from the top. The catalyst charge is about 60 ml and the remaining reactor volume is filled with inert material (glass spheres, porcelain rings, etc.). The liquid and gaseous products are separately analzyed by gas chromatography. The ammonia to cyclopentene ratio is 1.5.

TABLE 2

| Example No. | Catalyst | Temperature [°C.] | WHSV (g of starting material/h/g of catalyst) | Yield [%] |
|---|---|---|---|---|
| 40 | B | 270 | 0.7 | 5.6 |

We claim:

1. In a process for preparing an amine by the catalytic reaction of an olefin with ammonia, or a primary or secondary amine at elevated temperatures and pressures, the improvement which comprises:

contacting a mixture of the reactants in a reactor at an elevated temperature of from 200° to 400° C. and under a pressure of from 1 to 700 bar in the presence of a catalyst consisting essentially of an X-ray amorphous mesoporous catalyst, optionally including a microporous non-crystalline content, having the composition $$a\ MO_2 * b\ Q_2O_3 * c\ P_2O_5$$

were Q is at least one trivalent element selected from the group consisting of aluminum, boron, chromium, iron and gallium, M is at least one tetravalent element selected from the group consisting of silicon, titanium and germanium and the molar ratio of a:b is from 0.5:1 to 1000:1 and the molar ratio of c:b is from 0 to 2:1, the resulting non-crystalline catalyst having a specific BET surface area of from 200 to 1000 m²/g.

2. A process as claimed in claim 1 for preparing amines of the formula I

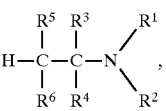

where $R^1, R^2, R^3, R^4, R^5, R^6$ are hydrogen, $C_1$- to $C_{20}$-alkyl, $C_3$- to $C_{20}$-cycloalkyl, $C_4$- to $C_{20}$-alkyl-cycloalkyl, $C_4$- to $C_{20}$-cycloalkyl-alkyl, aryl, $C_7$- to $C_{20}$-alkylaryl, $C_7$- to $C_{20}$-aralkyl and heterocyclic radicals, which comprises reacting olefins of the formula II

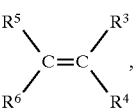

where $R^3$, $R^4$, $R^5$ and $R^6$ are as defined above, with ammonia or primary or secondary amines of the formula III

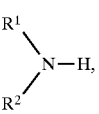

where $R^1$ and $R^2$ are as defined above.

3. A process for preparing amines as claimed in claim 2, wherein the catalysts IV used are prepared by hydrolysis of a synthesis mixture comprising water, optionally with a further solvent, one or more soluble, hydrolyzable Q compounds and one or more soluble, hydrolyzable M compounds.

4. A process as claimed in claim 1, wherein the non-crystalline catalyst of the formula IV is prepared from an amorphous gel of the catalyst components by means of the sol-gel method wherein the initially dried gel must be calcined in at least one step at a temperature of from 400° to 600° C.

5. A process as claimed in claim 4, wherein the element M is silicon and the element Q is boron.

6. A process as claimed in claim 4, wherein the element M is silicon and the element Q is aluminum.

7. A process as claimed in claim 4, wherein the olefin is reacted with ammonia in at least one continuous liquid phase reactor.

* * * * *